United States Patent [19]

Fry

[11] 4,130,574

[45] Dec. 19, 1978

[54] METHOD FOR INCREASING THE HYDROGEN:CARBON RATIO OF AN ORGANIC COMPOUND

[75] Inventor: James L. Fry, Toledo, Ohio

[73] Assignee: University of Toledo, Toledo, Ohio

[21] Appl. No.: 820,734

[22] Filed: Aug. 1, 1977

[51] Int. Cl.$^2$ .................. C07C 1/22; C07C 29/14; C07C 121/75

[52] U.S. Cl. .................. 260/465 F; 260/645; 260/650 R; 260/666 M; 260/666 P; 260/668 F; 260/668 R; 260/676 R; 260/682; 568/705; 568/835; 568/881; 568/907; 568/814; 568/648

[58] Field of Search .............. 260/465 F, 666 M, 682, 260/676 R, 668 R, 669 QZ, 618 H, 622 R, 631 R, 632 B, 638 R, 638 B, 612 D, 645, 650 R, 666 P, 668 F; 568/705, 835, 881, 907

[56] References Cited

PUBLICATIONS

Adlington et al., Tetrahedron Letters, No. 34, pp. 2955–2958, (1976).

*Primary Examiner*—Dolph H. Torrance

*Attorney, Agent, or Firm*—Edward L. Bailey; Vincent L. Barker, Jr.

[57] ABSTRACT

A method for increasing the hydrogen:carbon ratio of an organic compound is disclosed. The organic compound can be one having any of the following functions: hydroxyl, carbonyl, epoxide, acetal, ketal, hemiacetal and hemiketal. The method involves introducing the organic compound and a silicon hydride into a liquid which is either chemically inert or acidic and introducing $BF_3$ into the liquid to produce a reaction product having a higher hydrogen:carbon ratio than the starting organic compound. Examples of organic compound starting materials disclosed include undecanal, benzaldehyde, p-methylbenzaldehyde, p-chlorobenzaldehyde, p-methoxybenzaldehyde, p-cyanobenzaldehyde, p-nitrobenzaldehyde, 2-undecanone, cyclohexanone, 2-methylcyclohexanone, adamantanone, p-cyanoacetophenone, fluorenone, 1-naphthaldehyde, p-nitroacetophenone, fructose and cotton. The use, as the silicon hydride, of triethylsilane, (R)-(+)-1-naphthylphenylmethylsilane, dimethylethylsilane, phenylneopentylmethylsilane, and of tri-n-hexylsilane is disclosed, while methylene chloride is disclosed as the liquid in which the reaction is conducted.

3 Claims, No Drawings

METHOD FOR INCREASING THE HYDROGEN:CARBON RATIO OF AN ORGANIC COMPOUND

BACKGROUND OF THE INVENTION

The ability of organosilanes to transfer hydride selectively to a variety of carbocations is known, and has been utilized in the development of numerous synthetic techniques, e.g., the direct conversion of alcohols to hydrocarbons, which occurs when intermediate carbenium ions formed by reaction between alcohols and protic acids are captured by organosilanes. These known reactions are discussed in a paper* jointly authored by Merwyn G. Adlington, Michael Orfanopoulos and James L. Fry, and in the reference cited therein. The paper also describes briefly some of the experiments which constitute the genesis of the present invention.

*Tetrahedron Letters No. 34, pp. 2955–2958, 1976.

BRIEF DESCRIPTION OF THE INVENTION

Briefly stated, the present invention is based upon the discovery that the hydrogen to carbon ratio of certain organic compounds can be increased by a reaction involving a silicon hydride, a liquid which is either chemically inert or acidic and $BF_3$. The organic compound, to be capable of undergoing such reaction, must have at least one hydroxyl, carbonyl, epoxide, acetal, ketal, hemiacetal or hemiketal function. When the hydrogen:carbon ratio is increased in accordance with the invention, the increase can be the consequence of the reduction of, for example, a carbonyl group to a $CH_2$ group, or can be the consequence of the reduction of, for example, an aldehyde to the corresponding alcohol. The reaction appears to proceed stepwise, because whether a ketone, for example, is converted to an alcohol or to the corresponding hydrocarbon depends upon the proportions of $BF_3$ and of the silicon hydride used in carrying out the reaction, as well as upon the reaction time.

DETAILED DESCRIPTION OF PREFERRED EMBODIMENTS

The invention will be readily understood by those skilled in the relevant art from the following Examples, which are descriptions of reactions that have been conducted, and are presented solely for the purpose of illustrating and disclosing, but not of limiting, the invention.

EXAMPLE 1

An olefin believed to be E-2-undecene and n-undecane were produced from 5.00 g. 2-undecanone dissolved in 10 ml. methylene chloride by reaction with $BF_3$ gas in the presence of 11.24 g. triethylsilane. The reaction was conducted in a 100 ml. 3-neck flask to which was charged a 30 ml. portion of methylene chloride; thereafter the flask was fitted with a reflux condenser, a Claisen adapter with two addition funnels and a glass capillary which extended below the surface of the methylene chloride in the flask. The reflux condenser was cooled by a 2-propanol dry ice combination, and had a side tube exiting to a water trap. The 2-undecanone dissolved in methylene chloride was charged to one of the addition funnels, while the triethylsilane was charged to the other. An ice bath was placed around the reaction flask; stirring was commenced; and $BF_3$ gas was bubbled into the methylene chloride solution in the flask at a moderate rate sufficient that evolution of unreacted $BF_3$ from the reaction mixture could be observed. The ketone solution of 2-undecanone was then added to the flask over a period of a few minutes, followed by the silane, which was added in 3 minutes. Stirring and passage of $BF_3$ into the solution were continued for one hour, after which time the flow of $BF_3$ was stopped, and the reaction was quenched by addition of approximately 15 ml. saturated aqueous potassium carbonate solution to the reaction mixture. The organic material in the reaction mixture was extracted with diethyl ether, and the ether extract was washed with water, dried over sodium sulfate, and freed of volatile materials by means of a rotary evaporator at room temperature. The liquid which remained was purified by vacuum distillation at a temperature of 160°* and a pressure of 0.5 torr. The final yield was 4.40 g. product analyzed by vapor phase chromatography, nuclear magnetic resonance and infrared spectroscopy, and found to consist of 83 percent n-undecane and 17 percent of an olefin believed to be E-2-undecane on the basis of its infra-red absorption at 960 cm$^-$. The overall yield of the alkane, n-undecane, based upon the 2-undecanone charge, was 80 percent.

*All temperatures reported herein are in degrees C.

The procedure described above, or a modification where the ice bath was not employed, but the reaction was conducted, instead, under ambient conditions of about 20° C., has also been used to increase the hydrogen to carbon ratio of numerous other organic compounds. The compounds reacted, the number of equivalents, based upon compound reacted, of the triethylsilane, unless otherwise indicated, the reaction temperature, the reaction product, and yield data, for representative ones of these reactions are set forth in the following Table:

TABLE

| Organic Compound Reduced | Silane Equivalents | Reaction Temperature | Reaction Time Minutes | Percent Yield of Product(s) RCH(OH)R' | Percent Yield of Product(s) RCH$_2$R' |
|---|---|---|---|---|---|
| Undecanal | 1.5 | 0° | 10 | 92 | |
| Benzaldehyde | 18 | 25° | 11 | | 52 |
| p-Methylbenzaldehyde | 7 | 25° | 6 | | 45 |
| p-Chlorobenzaldehyde | 9 | 25° | 10 | | 72 |
| p-Methoxybenzaldehyde | 2 | 25° | 10 | | 100 |
| p-Cyanobenzaldehyde | 3 | 25° | 10 | 100 | |
| p-Nitrobenzaldehyde | 1.5 | 25° | 5 | 100 | |
| Cyclohexanone | 2 | 25° | 1.5 | 82 | |
| Cyclohexanone | 4 | 25° | 30 | | 90 |
| 2-Methylcyclohexanone | 2.2* | 25° | 60 | | 88 |
| Adamantanone | 8 | 25° | 30 | | 80 |
| p-Cyanoacetophenone | 3 | 25° | 10 | 100 | |
| p-Nitroacetophenone | 4 | 25° | 3 | 100 | |
| p-Nitroacetophenone | 4 | 25° | 30 | | 100 |
| Benzyl Alcohol | 8 | −70° | 5 | | 40 |
| 2-Octanol | 1.2 | 0° | 75 | | 58 |

TABLE-continued

| Organic Compound Reduced | Silane Equivalents | Reaction Temperature | Reaction Time Minutes | Percent Yield of Product(s) | |
|---|---|---|---|---|---|
| | | | | RCH(OH)R' | RCH$_2$R' |
| 1-Adamantanol | 1.3 | 25° | 20 | | 100 |
| 2-Adamantanol | 1.3 | 25° | 15 | | 98 |
| 2-Phenyl-2-Pentanol | 1.1** | −60° | 5 | | 82 |
| 2-(p-Nitrophenyl)-2-butanol | 1.1*** | 0° | 15 | | 100 |

*Dimethylethylsilane.
**(R)-(+)-1-naphthylphenylmethylsilane.
***Phenylneopentylmethylsilane.

Fructose and cotton have also been reacted with BF$_3$ in the presence of triethylsilane by substantially the procedure described in Example 1. In each case, the presence of hexane in the reaction product was established by gas chromotography. Such reaction has also been used to react 1-naphthaldehyde and fluorenone to produce, respectively, 1-methylnapthalene and fluorene, as well as to react stilbene oxide.

It will be apparent from the data presented above that the instant invention provides a simple reaction by means of which the hydrogen:carbon ratio of various organic compounds, provided that they have functionality as set forth above, can be increased, and that the reaction conditions are not critical. For example, the reaction time has been conducted at temperatures ranging from −70° to 25°, and it is believed that temperatures at least as high as 200° would be operable. Similarly, while the reactions reported above have all been conducted at atmospheric pressure of substantially one bar, it is believed that either higher or lower pressures could be employed ranging, for example, up to about 1000 psi. The reaction of organic compounds having the ketone, aldehyde, hydroxyl and epoxide function has been specifically described. Compounds having the acetal the ketal, the hemiacetal and the hemiketal function all react in the presence of BF$_3$ to form an aldehyde or ketone function and are, therefore, equivalent as starting materials. This is demonstrated by the identification of hexane when fructose and cotton were reacted with BF$_3$ in the presence of triethylsilane by substantially the procedure described in Example 1.

It will be apparent from the foregoing examples of silanes in the presence of which the reaction of the instant invention proceeds that any silicon hydride, i.e., any silicon compound having at least one hydrogen attached directly to silicon, can be used to cause the reaction to proceed. It is believed that the great affinity of silicon for fluorine is responsible for the general operability of silicon hydrides, and for the reason that this affinity enables them, in effect, to sequester fluorine from the BF$_3$ reactant and consequently to release hydrogen for reaction with the organic compound.

The data presented above indicate that the use of a comparatively long reaction time and a comparatively large number of silane equivalents favors the production of hydrocarbons, while the use of a comparatively short reaction time and of a comparatively lesser number of silane equivalents favors the termination of the reaction at an intermediate, e.g., alcohol, stage. Ordinarily, it is desirable to use at least one silane equivalent, based upon the organic compound, to enable complete reaction. On the other hand, there is usually no reason to use more than about ten silane equivalents, although, disregarding possible waste of silane raw material, a greater excess does not appear to be detrimental. Ordinarily, reaction proceeds as far as it is capable of proceeding in not more than about 60 minutes, and reaction is frequently complete in as few as ten minutes. Reaction times of at least about one minute are usually preferred.

The reaction according to the invention should be carried out under such conditions of temperature and pressure that both the silicon hydride and the liquid in which the reaction is conducted exist in the liquid phase. This makes −95° about the minimum temperature that can be employed when methylene chloride is the liquid (freezing point −96.7°), and necessitates either the use of a liquid reaction medium which freezes at a temperature lower than methylene chloride or the use of superatmospheric pressure if silane (SiH$_4$, boiling point −112° at 760 millimeters Hg pressure) is used as the silicon hydride. The best mode contemplated for practicing the method of the invention involves the use of superatmospheric pressure. For example, the organic compound to be reacted, e.g., cotton, the reaction liquid, e.g., methylene chloride, and a suitable catalyst,* e.g., palladium, can be charged to an autoclave lined with polytetrafluoroethylene and equipped with at least one valved inlet; after sealing of the autoclave with a cover, also lined with polytetrafluoroethylene, silane is introduced into the autoclave through the inlet to develop sufficient pressure within the autoclave to cause solution of the silane in the methylene chloride or the like. The reaction can be conducted at ambient temperature of about 25°, but elevated temperatures up to about 200° can be employed, if desired, to increase the rate of reaction. Ordinarily, there is no point in removing heat from the system to lower the temperature thereof below about 25°. The amount of silane introduced into the autoclave can range from perhaps 0.01 to 0.1 equivalent, based upon the organic material charged. BF$_3$ is then introduced into the autoclave, for example in an amount substantially equivalent to the previously charged silane. As reaction proceeds, silicon tetrafluoride is formed from the silane, and B$_2$O$_3$ is formed from the boron trifluoride. This reaction causes a reduction in pressure within the autoclave, so that progress of the reaction can be monitored on the basis of autoclave pressure. When the pressure drops sufficiently to indicate substantial reaction of the silane and BF$_3$, hydrogen is introduced into the autoclave; in the presence of the palladium or other suitable catalyst, hydrogen reacts with silicon tetrafluoride, forming silane and hydrogen fluoride; the latter reacts with the previously formed B$_2$O$_3$, regenerating the BF$_3$ required to cause further reaction between the silane and the organic compound, which can again be monitored on the basis of pressure. Repeated additions of hydrogen can be made until reaction is indicated to be complete by the maintenance of a substantially constant pressure within the autoclave following a hydrogen addition. The autoclave can then be vented and opened, and the desired hydrocarbon recovered in a conventional manner, e.g. by filtration and distillation, from the other components of the reaction mixture for a subsequently described reaction.

It will be apparent that various changes and modifications can be made from the specific details set forth herein without departing from the spirit and scope of the invention as defined in the appended claims.

What I claim is:

1. A method for increasing the hydrogen to carbon ratio of an organic compound having at least one hydroxyl, carbonyl, epoxide, acetal, ketal, hemiacetal or hemiketal function, said method comprising introducing the organic compounds and a silicon hydride into a liquid which is either chemically inert or acidic and introducing $BF_3$ into the liquid to produce a reaction product having a higher hydrogen to carbon ratio than the starting organic compound.

2. A method as claimed in claim 1 wherein the reaction is conducted at a superatmospheric pressure.

3. A method as claimed in claim 2 wherein the reaction is conducted at a temperature between 25° and 200°.

UNITED STATES PATENT OFFICE
CERTIFICATE OF CORRECTION

Patent No. 4,130,574     Dated December 19, 1978

Inventor(s) James L. Fry

It is certified that error appears in the above-identified patent and that said Letters Patent are hereby corrected as shown below:

Col. 2, Line 37; "$cm^-$" should be ... $cm^{-1}$

Col. 3, Line 25; "reaction time has" should be -- reaction has

*Signed and Sealed this*

*Twelfth* Day of *June 1979*

[SEAL]

Attest:

RUTH C. MASON
*Attesting Officer*

DONALD W. BANNER
*Commissioner of Patents and Trademarks*